(12) United States Patent
Macchi

(10) Patent No.: US 10,842,434 B2
(45) Date of Patent: Nov. 24, 2020

(54) DEVICE FOR CONTROLLING THE INTAKE OF DRUGS, SYSTEM FOR SIGNALING AND CONTROLLING THE INTAKE OF DRUGS

(71) Applicant: AMIKO S.R.L., Milan (IT)

(72) Inventor: Fausto Macchi, Vermezzo (IT)

(73) Assignee: AMIKO S.R.L., Milan (IT)

( * ) Notice: Subject to any disclaimer, the term of this patent is extended or adjusted under 35 U.S.C. 154(b) by 1377 days.

(21) Appl. No.: 14/891,083

(22) PCT Filed: May 15, 2014

(86) PCT No.: PCT/EP2014/059945
§ 371 (c)(1),
(2) Date: Nov. 13, 2015

(87) PCT Pub. No.: WO2014/184293
PCT Pub. Date: Nov. 20, 2014

(65) Prior Publication Data
US 2016/0113568 A1   Apr. 28, 2016

(30) Foreign Application Priority Data

May 16, 2013   (IT) .............................. CO2013A0017

(51) Int. Cl.
*G08B 1/08*   (2006.01)
*A61B 5/00*   (2006.01)
(Continued)

(52) U.S. Cl.
CPC .......... *A61B 5/4833* (2013.01); *A61B 5/0022* (2013.01); *A61B 5/6801* (2013.01);
(Continued)

(58) Field of Classification Search
None
See application file for complete search history.

(56) References Cited

U.S. PATENT DOCUMENTS 8,229,758 B2 * 7/2012 Moncrease ......... G06F 19/3456
705/2
8,571,835 B2 * 10/2013 Farrow ............... G01P 15/0891
307/400
(Continued)

FOREIGN PATENT DOCUMENTS

WO        98/49659 A2   11/1998
WO     2012/109229 A2    3/2012

OTHER PUBLICATIONS

International Search Report for PCT/EP2014/059945 dated Nov. 9, 2014 Oct. 24, 2013 (5 pages).

*Primary Examiner* — Julie B Lieu
(74) *Attorney, Agent, or Firm* — King & Schickli, PLLC

(57) ABSTRACT

Device (1) for controlling the intake of drugs, applicable to a package (50) containing one or more doses of a drug, said device (1) comprising: sensor means (21) adapted to detect the vibrational energy transferred to said package (50), in response of interactions of a user with said package (50) to release one or more doses of said drug; a processor (25) connected to said sensor means (21); wherein said processor (25) is configured to calculate intake information of said drug on the basis of the vibrational energy detected by said sensor means (21); system for signalling the intake of drugs; system (100) for controlling the intake of drugs and drug accessories (10, 20, 30, 40, 40b) comprising such device (1) applicable to drug packages.

21 Claims, 16 Drawing Sheets

(51) Int. Cl.
*G06F 19/00* (2018.01)
*A61J 7/04* (2006.01)
*A61J 1/03* (2006.01)
*A61M 15/00* (2006.01)
*A61M 5/315* (2006.01)

(52) U.S. Cl.
CPC .......... *A61B 5/6887* (2013.01); *A61B 5/7278* (2013.01); *A61J 1/035* (2013.01); *A61J 7/049* (2015.05); *A61J 7/0418* (2015.05); *A61J 7/0436* (2015.05); *A61J 7/0481* (2013.01); *A61M 5/31535* (2013.01); *A61M 5/31556* (2013.01); *A61M 5/31566* (2013.01); *A61M 5/31573* (2013.01); *A61M 5/31593* (2013.01); *A61M 15/003* (2014.02); *A61M 15/008* (2014.02); *A61M 15/0065* (2013.01); *A61M 15/0083* (2014.02); *G06F 19/3456* (2013.01); *G06F 19/3462* (2013.01); *A61B 2560/0475* (2013.01); *A61B 2562/028* (2013.01); *A61B 2562/0219* (2013.01); *A61J 2200/30* (2013.01); *A61M 15/0035* (2014.02); *A61M 15/0041* (2014.02); *A61M 2202/064* (2013.01); *A61M 2205/332* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/582* (2013.01); *G06F 19/3468* (2013.01)

(56) References Cited

U.S. PATENT DOCUMENTS

| | | | |
|---|---|---|---|
| 2003/0189492 A1* | 10/2003 | Harvie | A61M 16/0051 340/573.1 |
| 2010/0100391 A1* | 4/2010 | Daya | G16Z 99/00 705/2 |
| 2010/0240962 A1* | 9/2010 | Contant | A47G 21/02 600/300 |
| 2010/0305975 A1* | 12/2010 | Daya | G06F 19/325 705/3 |
| 2011/0169635 A1 | 7/2011 | Johnson | |
| 2011/0295215 A1* | 12/2011 | Nielsen | G16H 20/17 604/257 |
| 2011/0313395 A1* | 12/2011 | Krulevitch | A61M 5/24 604/504 |
| 2012/0004637 A1* | 1/2012 | Krulevitch | A61M 5/315 604/504 |
| 2012/0183941 A1 | 7/2012 | Steinmetz | |
| 2013/0172690 A1* | 7/2013 | Arne | A61M 15/009 600/301 |
| 2014/0188426 A1* | 7/2014 | Fastert | G01P 15/0891 702/139 |
| 2019/0192779 A1* | 6/2019 | Nagar | B01L 3/0293 |
| 2019/0238360 A1* | 8/2019 | Laskowitz | H04L 12/2827 |
| 2020/0023139 A1* | 1/2020 | Streit | A61M 5/31568 |

\* cited by examiner

DEVICE FOR CONTROLLING THE INTAKE OF DRUGS, SYSTEM FOR SIGNALING AND CONTROLLING THE INTAKE OF DRUGS

RELATED APPLICATIONS

This application is a national phase of Application No. PCT/EP2014/059945 filed May 15, 2014, and claims priority from Italian Patent Application No. CO2013A000017 filed May 16, 2013, both incorporated by reference in their entirety.

FIELD OF TECHNOLOGY

The present invention refers to a device applicable to drugs packages for controlling and signaling intake thereof, a system for signaling and controlling drugs intake.

BACKGROUND

Many patients have to assume drugs prescribed for their cure, according to the dosage assigned by their medical practitioner.

Drugs intake control allows to establish the suitability of a cure assigned to a certain patient. The term adherence to the prescription or therapy indicates if a patient has assumed the drugs according to the dosage assigned. A full adherence to the prescription reflects the fact that the patient has assumed the drugs assigned in full accordance to the dosage assigned or during the prescribed time/period in the day, at the assigned time. A low adherence to the prescription reflects the fact that the patient not always has assumed the drugs in accordance to the dosage assigned. For example, a medical practitioner may prescribe a dosage of three tablets per day, to be taken in three different moments of the day, for two days. A patient who takes all the three tablets, in the three different moments, for each day of the two prescribed for the cure, has a full adherence to the prescription. A patient who skips taking some of the tablets, has a low adherence; how much the adherence is low depends on how many assumption the patience has skipped. In some cases, it is also important to know the adherence to the right moment in the day in which each dosage has to be assumed.

Thus, a medical practitioner who knows the adherence of a patient to the prescription, may evaluate the cure or therapy assigned more properly. To record the adherence to the prescription, a patient may use different methods.

He may use his memory, trying to remember if has taken each drug of the prescription. Otherwise, he may transcript on a paper sheet each assumption and thus establish ex post if he skipped one or more assumption.

On the other hand, some devices have been developed to signal a voice of assumption of a drug. Once the patient has set the dosage assigned, a buzzer provided in device signals him, emitting a sound, to assume the drug. In one example, the device is a tablet box for containing the drugs, and integrates a programmable electronic device which signals and verifies the assumption of the drug contained. To do this, the electronic device comprises a sensor connected to the opening mechanism of the tablet box and signaling means. After putting the drugs to take in the tablet box and programming the dosage, the signaling means alert the patient, and the sensor detects if the opening mechanism is actually opened and then closed. From this series of actions—alerting the patient and detecting the actual opening and closing of the mechanism—the device deems the assumption occurred. In a different order, or if the opening and closing is skipped, the device iterates the signaling, until the patient carries out the correct order of procedure, or stops the signaling.

The patient has to program the electronic device and put the drug in the box very carefully. An error in this operation would cause problems in the assumption of drugs.

SUMMARY OF THE INVENTION

The Applicant noted that the devices and techniques known from the state of the art do not allow to obtain a reliable device for controlling the intake of drugs.

The approaches in which the patient uses his memory or where he records on a paper sheet every assumption, are unreliable. If he wrongly remembers or transcripts one or more assumptions, he may take wrong initiatives or report to his medical practitioner wrong data.

The use of the tablet box with the electronic device partly overcome these drawbacks. However such device requires a preparatory activity from the patient; to be conducted with great care and in any case with high probability of error.

This situation is particular disadvantageous for both patients and medical practitioners. The firsts have no aid for controlling and verifying drugs intake, the latters have no tools with which verify the adherence of the patients and thus determine if the cure prescribed was ineffective due to a low adherence.

A first object of the present invention is to realize a device for controlling the intake of drugs which overcome the drawbacks of the devices known from the prior art in a simple and economic way.

A second object of the present invention is to realize a device by which is possible to determine if a drug (or one or more doses of a drug) may be actually deemed assumed by a patient.

A third object of the present invention is to provide medical practitioners a reliable aid to determine the adherence to the cure of their patients.

The inventive idea of the present invention is to sense the energy that a user transfers to a drug package when he interacts with the package to perform actions aimed to release one or more doses of the drug to release.

In general, a device for controlling the intake of drugs according to the present invention is applicable to a package containing one or more doses of a drug, and comprises:
 sensor means adapted to detect vibrational energy transferred to said package, in response of interactions of a user with said package to release one or more doses of said drug;
 a processor connected to the sensor means;
wherein the processor is configured to calculate intake information of the drug on the basis of the vibrational energy detected by the sensor means.

A further aspect of the present invention relates to a system for signalling the intake of drugs, comprising:
 a device according to the present invention, in particular comprising communication means;
 a signaling device comprising signaling means and communication means;
wherein the processor of the control device is configured to transmit intake information by means of the communication means of the device to the signaling device;
and wherein the signaling device is adapted to receive intake information by means of its communication means and to signal items of the intake information by means of its signaling means.

Another aspect of the present invention relates to a system for controlling actions related to the intake of drugs, comprising:
- a device according to the present invention, in particular comprising communication means;
- an electronic programming computer configured to generate dosage information related to a patient and to transmit said information to said device;
- a remote server configured to receive, in particular through a public computer network, and to store said dosage information from said electronic programming computer and said intake information from said device;
- an electronic computer configured to communicate with the remote server, in particular through a public computer network, and to access said dosage information and said intake information.

Aspects of the present invention further relates to drugs package and drugs dosing package accessories.

In particular, a tablet blister accessory comprising a device according to the present invention, wherein the sensor means of the device are adapted to detect vibrational energy transferred to the drug blister when a user extracts a tablet from the blister, in particular when said user transfers energy to said blister to tear the foil covering a tablet.

In particular, a tablet bottle accessory comprising a device according to the present invention, wherein the sensor means of the device are adapted to detect vibrational energy transferred to the tablet bottle when a user extracts a tablet from the bottle.

In particular, a liquid drug injection pen accessory comprising a device according to the present invention, wherein the sensor means of the device are adapted to detect vibrational energy transferred to the pen when a user acts on the pen in order to set at least one drug dose and dispense said at least one drug dose.

In particular, a drug inhaler accessory comprising a device according to the present invention, wherein the sensor means of the device are adapted to detect vibrational energy transferred to the inhaler when a user acts on the inhaler in order to set a drug dose and dispense said drug dose.

LIST OF THE DRAWINGS

FIGS. from 19 to 22 show another embodiment of a device according the present invention.

DETAILED DESCRIPTION OF THE INVENTION

The following description of exemplary embodiments refer to the accompanying drawings. The same reference numbers in different drawings identify the same or similar elements. The following detailed description does not limit the invention. Instead, the scope of the invention is defined by the appended claims.

Further, the particular features, structures or characteristics may be combined in any suitable manner in one or more embodiments.

Figure 1:
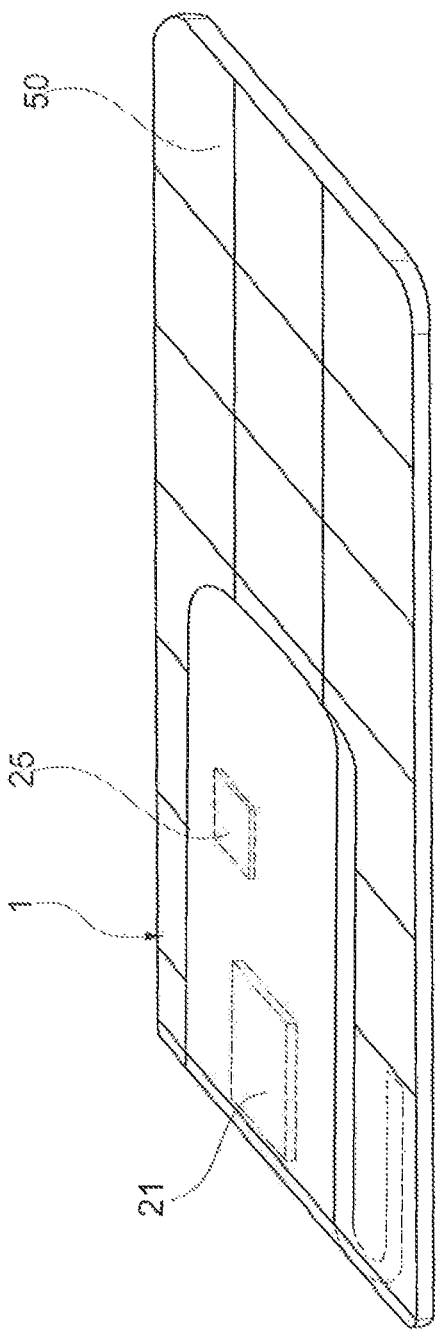
FIG. 1 shows a perspective view of a device according the present invention applied to a drug package.

FIG. 1 shows an embodiment of a device 1 for controlling the intake of drugs, applicable to a package 50 containing one or more doses of a drug. The package 50 may be any package suitable for containing one or (typically) more doses of a drug. As will be clearer afterward, according to the present invention, the package 50 may also comprise a drug dispensing package, namely a package for a drug serving also as a dose(s) dispenser of the same drug. The device 1 comprises:
- sensor means 21 adapted to detect vibrational energy transferred to the package 50, in response of interactions of a user with the package 50 to release one or more doses of said drug. Such interaction of a user with the package 50, aimed at releasing one or more doses of drug contained, results in an application of forces to the package 50. The application of these forces (or the resulting force) causes a transfer of energy from the user to the package. For example, if the package 50 is a tablet blister, there is some energy transferred to the package due to the moving of the package, and some energy (transferred to the package) for tearing the lidding foil (typically made in aluminum) covering each tablet.

According to the present invention, the package 50 is intended as all that surrounds for containing the drug—composed by the excipients and the active substance—actually assumed by the patient. Such package 50 may assume various forms, according to the type of drug for which is designed.

The device 1 further comprises a processor 25 connected to the sensor means 21. The processor 25 is configured to calculate intake information of the drug on the basis of the vibrational energy detected by said sensor means 21. The processor 25 is configured to calculate intake information of the drug on the basis of the vibrational energy detected by said sensor means 21.

Intake information reports if one or more doses of a drug may be deemed assumed from the patient. The intake information may be recorded in various ways. According to one embodiment, the intake information may consist of an array having a plurality of records, each record for one dose of the drug that a patient has to assume. For example, if he/she has to take 2 doses per day for two days, the intake information will have 4 records. According to this embodiment, each record will be populated according to the outcome of the assumption procedure of the patient. Thus, each record reports if the corresponding dose of drug may be deemed assumed from the patient, or otherwise, not. In one example, the "assumed drug coding" may be the following: if the dose of drug may be deemed assumed, the record the intake information array is set as "1", otherwise will be set as "0".

Figure 2:
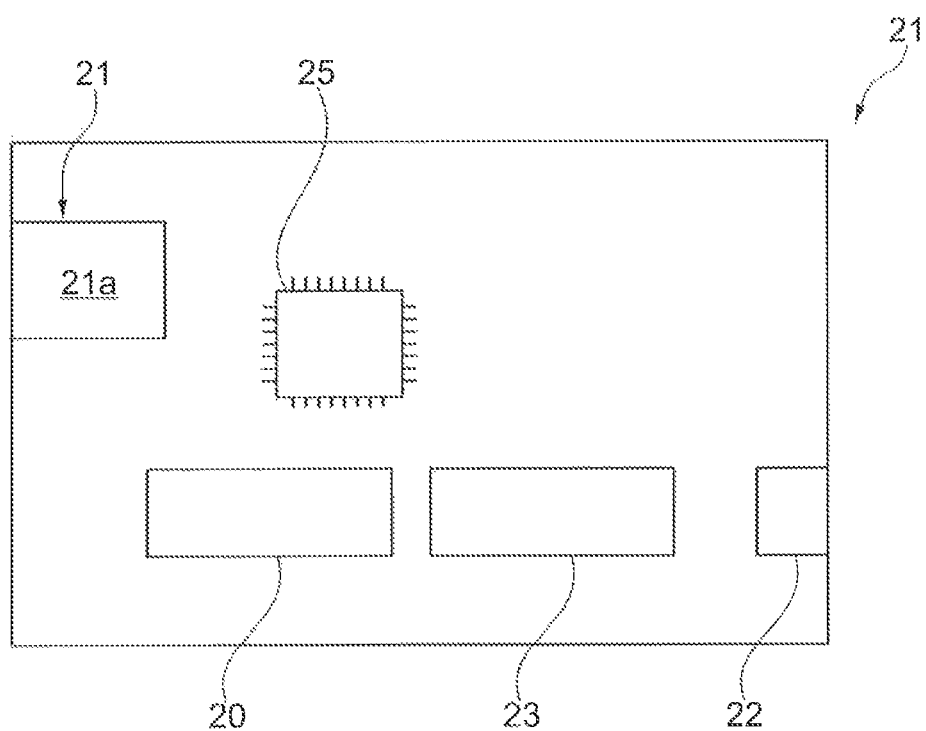
FIG. 2 shows a schematic view of a first embodiment of the logical architecture of a device according the present invention.

FIG. 2 shows a schematic view of the logic architecture of a device 1 according to the present invention. In this embodiment, the sensor means 21 comprise at least one accelerometer 21 *a* implemented as a micro-electro-mechanical system, or MEMS. In particular, the accelerometer 21 *a* is a tri-axial accelerometer. Such accelerometer detects the accelerations on the three axes, X, Y and Z. As known, the energy may be derived from the acceleration detected by an accelerometer. From the acceleration provided by the accelerometer 21 *a* is thus possible to derive the vibrational energy transferred to package 50.

According to one embodiment, the device 1 further comprises:

First storage means 20 adapted to store dosage information of the drug, wherein the dosage information are related to a patient.

First communication means 22, in particular for proximity communications, adapted to receive the dosage information.

Second storage means 23 adapted to store the intake information of the drug by said patient, calculated by the processor 25.

Dosage information reports the dosage of the drug assigned by the medical practitioner (or by the patient himself or by a relative or by a pharmacist). These information are relative to a patient. According to one embodiment, the dosage information may consist of an array having a plurality of records, each record is an item of dosage, thus represents the dose of drug that a patient has to assume. For example, if he/she has to take 2 doses per day for two days, the intake information will have 4 records. In one embodiment, each record may be populated with a progressive identifier of the dose of drug to which it refers. Furthermore, in another embodiment, each record may also comprise time data indicative of the time in which the assumption is expected, and may be—for example—in form of a timestamp associated to each record. For example, the first dose to assume in the day has the time stamp "9:30 AM" associated, and so on.

In one embodiment, the number of records of the dosage information array corresponds to the number of records of the intake information array. In this way, a link between a record of the dosage information (corresponding to an item of dosage of a drug) and the corresponding record of the intake information array may be created. In the case in which the patient skipped assuming one or more doses prescribed, the exact dose(s) skipped may be quickly retrieved checking which record of the intake information is set as "0" (according to the "assumed drug coding" previously described).

In one embodiment, the processor 25 of the device 1 is configured to receive the dosage information, by means of said first communication means 22, from an electronic programming computer 70. Such first communication means 22 are in particular for proximity communications. In one embodiment, such first communication means 22 may be means for NFC communications. In another embodiment, may be means for Bluetooth communications.

The medical practitioner (or the pharmacist) set the dosage information on the device 1 via a programming computer, according the prescribed therapy. The patient then receives the device 1 programmed. The patient in turn applies the device 1 to the package 50 containing one or more doses of the drug he/she has to assume. The processor 25 is configured to calculate intake information, as will also be described in more detail below, on the basis of the vibrational energy detected by the sensor means 21, in response of interactions of a user with said package 50 to release one or more doses of the drug.

Figure 3:
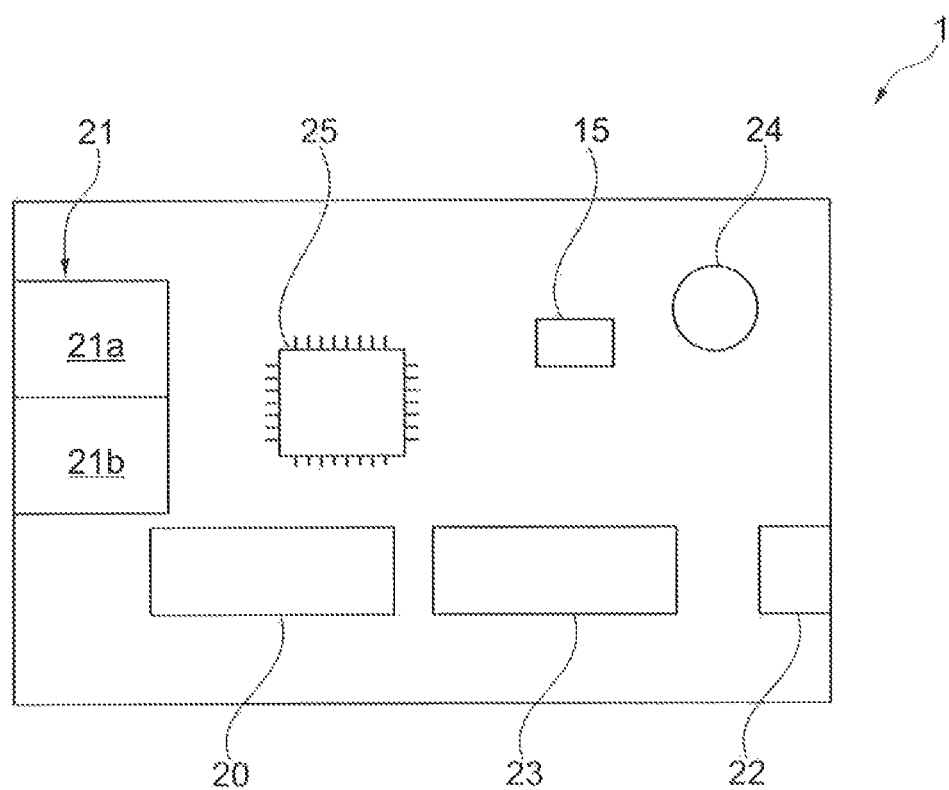
FIG. 3 shows a schematic view of a second embodiment of the logical architecture of a device according the present invention.

FIG. 3 shows an embodiment of a device 1 according the present invention. The sensor means 21 of the device 1 further comprise a gyroscope 21 *b*, in particular a gyroscope implemented as a micro-electro-mechanical system, or MEMS. The device 1 comprises signaling means 15 connected to the processor 25. According to this embodiment, the processor 25 is further configured to signal an item of the dosage information via the signaling means 15. In one embodiment, a record of the dosage information triggers off the processor 25 to calculate intake information, in particular to calculate and store the value of the flag in the corresponding record of the intake information array.

In one embodiment, the processor 25 is further configured to iterate the signaling of said item of said dosage information on the basis of the intake information calculated. In particular, if from intake information calculated may be inferred that the assumption of a dose of drug did not occur, the processor 25 may iterate the signaling to remember the patient to assume that dose of drug. Furthermore, according to one embodiment, the device 1 further comprises second communication means 24. These second communication means 24 may comprise a Wi-Fi chipset. According to this embodiment, the processor 25 is further configured to transmit the dosage information and the intake information to a remote server 80, by means of the second communication means 24, in particular via a public information network NW, for example by means of the Wi-Fi chipset via the Internet. An authorized user (for example the patient or the medical practitioner of the patient or a relative of the patient) may access the intake information on the remote server 80.

Figure 4:
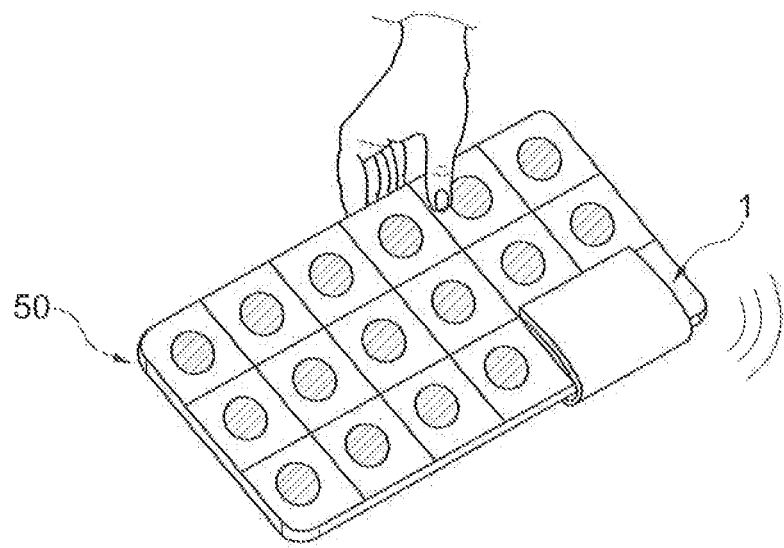
FIG. 4 shows a perspective view of an embodiment of device according the present invention applied to a drug blister.

FIGS. from 4 to 6 show a device 1 applied to package 50 containing a plurality of doses of a drug. The package 50 in these figures is a tablet blister. In FIG. 4, upon signaling of the device 1, the user takes the package 50 and start interacting with the package 50 to release one dose of drug. The accelerometer 21*a* of the device 1 (not shown in FIG. 4) starts detecting vibrational energy due to these first interactions.

Figure 5:
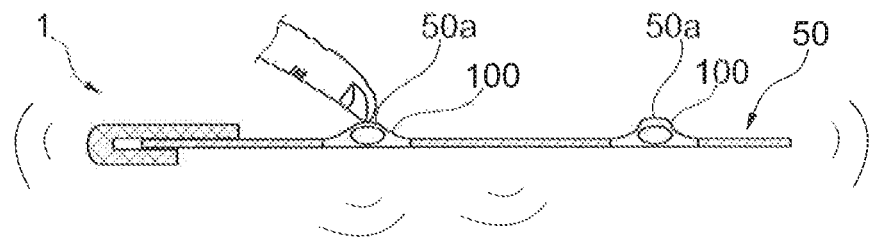
FIG. 5 and FIG. 6 show interactions of a user with a drug blister to extract a tablet.

In FIG. 5, the user applies a force aimed at tearing the foil 50*a* covering the tablet 100. In response to this interactions, the accelerometer 21*a* of the device 1 detects the corresponding vibrational energy transferred to package 50.

Figure 6:
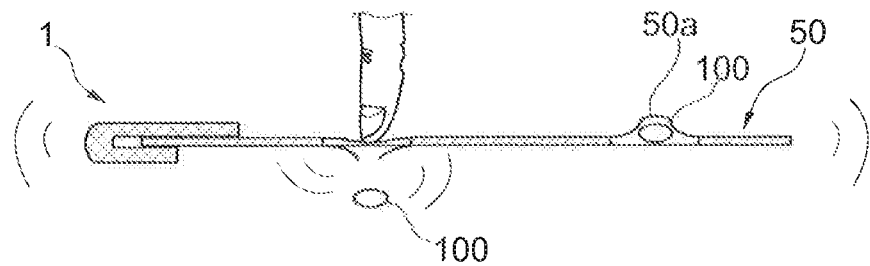

As shown in FIG. 6, when the force applied by the user is sufficient to tear the lidding foil 50*a*, the tablet 100 is released. The accelerometer 21a keeps detecting the corresponding vibrational energy transferred to package 50.

A user interacts with a package and thus transfers energy in a certain way, depending on the type of package containing the drug. In particular, depending on the shape and structure of the package. A certain vibrational energy is transferred to the package if a tablet has to be extracted from the blister. A different vibrational energy is transferred in case of a dose of liquid drug assumed using an injection pen (that is also the package of the liquid drug). To this end, the dosage information comprise package information relative to the type of package containing said one or more doses of a drug.

In one embodiment, the processor 25 is configured to obtain from the accelerometer 21a the vibrational energy detected in a time lapse. Furthermore the processor 25 is configured to calculate intake information also on the basis of package information. The processor 25 is further configured to set the time lapse in which obtains vibrational energy from the accelerometer 21a on the basis of package information.

Figure 7:
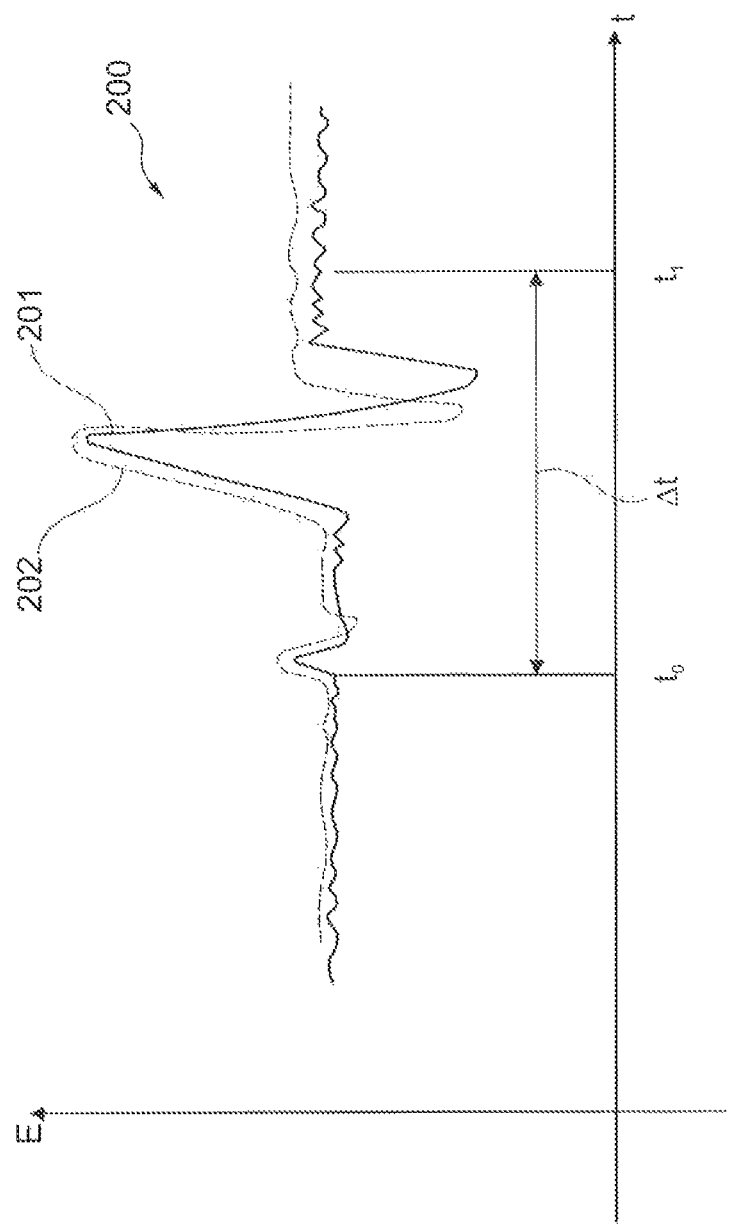
FIG. 7 shows a diagram of the vibrational energy detected by the device in response to interactions of the user of FIGS. 5 and 6.

FIG. 7 shows a diagram 201 of the vibrational energy transferred to the package 50 of the example represented in FIGS. from 4 to 6, detected from the accelerometer 21a. In one embodiment, intake information are calculated comparing the values of the vibrational energy detected with samples values, stored on device. In FIG. 7, a reference diagram 202 of the expected vibrational energy transferred to the package 50 is superimposed to the diagram 201 of the energy detected.

In one embodiment, the flow to calculate intake information is the following. The accelerometer 21a of the device 1 detects the vibrational energy transferred to the package 50. The record of the dosage information, signalling the patient, further triggers off the processor 25 that starts calculate intake information. In particular, the processor 25 sets a time lapse Δt in which obtains the vibrational energy transferred to the package 50 detected by the accelerometer 21a. This time lapse is set on the basis of package information, and thus may vary accordingly. The processor 25 thus obtains vibrational energy data, represented in the diagram 201.

This data are used from the processor 25 to calculate intake information. In particular, on the basis of package information, the processor 25 is configured to establish which sample values use for comparing the vibrational energy data detected.

In one embodiment this comparison is carried out assessing the difference between absolute value of data of the reference diagram and data of the vibrational energy detected. If this difference reaches a certain threshold, the dose of drug may be deemed assumed, otherwise may be deemed not assumed. The record of the intake information array is assigned correspondingly.

Some packages have to be moved and rotated in a determined manner to assume the drug contained. To this end, according to an embodiment, the sensor means comprise a gyroscope 21 b, in particular implemented as a micro-electro-mechanical system, or MEMS. The gyroscope 21 b is adapted to provide orientation information on the orientation of the package 50. In this way, orientation information provided by the gyroscope may be used to complete and sum up information provided by the accelerometer. Orientation information may be provided in various formats and with a certain frequency in time. The processor 25 is configured to process orientation information to establish if the package 50 has been moved and rotated. According to an embodiment, the processor 25 is configured to combine orientation information with package information to check if the movement and rotations detected are proper for package to which they refer.

Furthermore, the processor 25 is configured to calculate intake information on the basis of the vibrational energy detected by the accelerometer and the orientation information.

In particular, according to an embodiment, the processor 25 is configured to evaluate the vibrational energy detected by the accelerometer and the orientation information on the basis of the package information. In other words, from package information the processor 25 may infer if to assume a dose of a drug, the relative package has to be moved and rotated in a determined manner. For example, the drug inhaler for assuming a powder drug has to be moved and rotated to be charged, and rotated again to assume the drug. From the orientation information may be derived if these movements and rotations have been performed. The processor 25 may also be programmed to discard vibrational energy detected by the accelerometer on the basis of the orientation information. If analyzing the orientation information may be deducted that assumption couldn't have occurred, may be also deducted that the vibrational energy detected refers, for example, to displacement of the package and not to interactions of the user with the package to release one or more doses of the drug.

Figure 8:
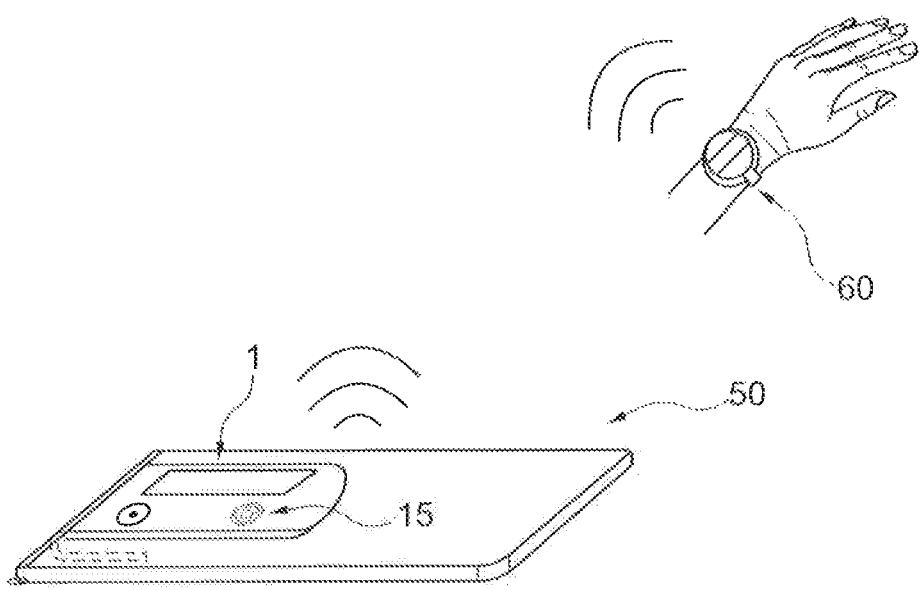
FIG. 8 shows an embodiment of a system for signaling the intake of drugs.

FIG. 8 shows an embodiment of a system for signalling intake of drugs comprising:
- a device 1 as described above, in particular comprising communication means 22, 24;
- a signaling device 60 comprising signaling means and communication means.

The signaling device 60 is adapted to receive dosage information by means of its communication means. It is further adapted to signal items of the dosage information by means of its signaling means.

According to an embodiment, the device 60 comprises or consists of an element wearable by said patient, for example a wrist bracelet. The communication between the device 1 and the signaling may be a proximity communication, in this case only proximity communication means are involved. Otherwise, a point to point communication via the Internet between the device 1 and the signaling device 60 may take place.

Figure 9:
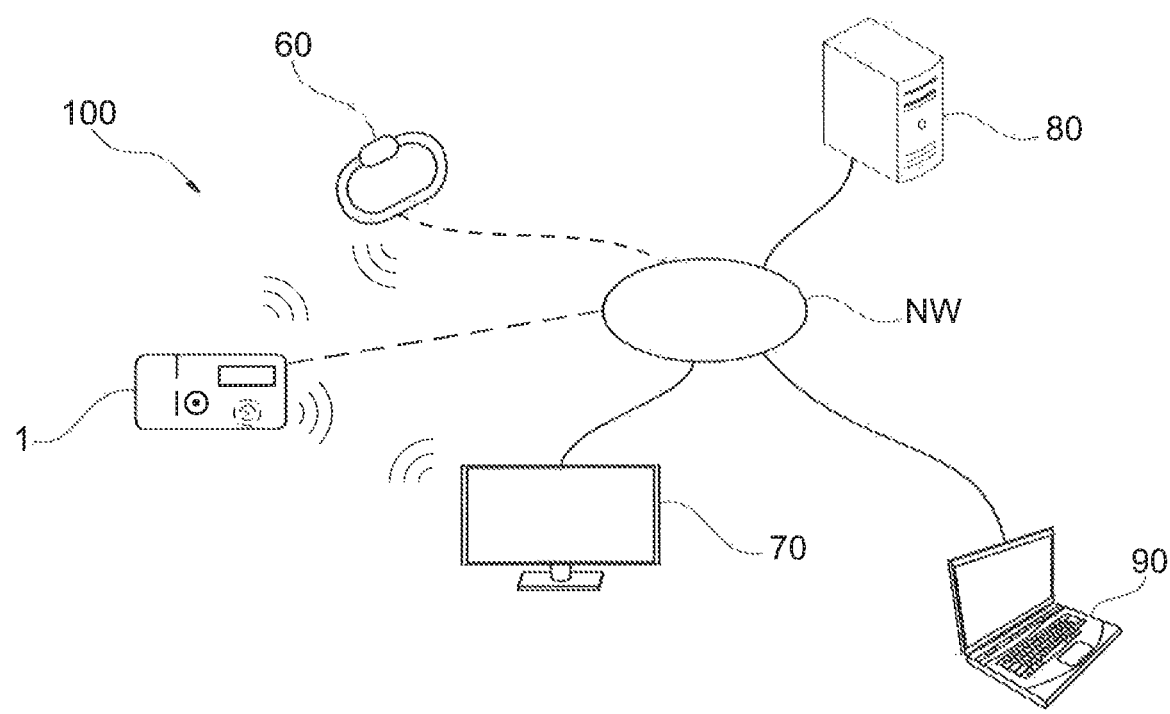
FIG. 9 shows an embodiment of a system for controlling actions related to the intake of drugs.

FIG. 9 shows an embodiment of a system 100 for controlling actions related to the intake of drugs. Such a system comprises:
- a device 1 as described above, in particular comprising communication means 22, 24;
- an electronic programming computer 70 configured to generate dosage information related to a patient and to transmit the information to the device 1;
- a remote server 80 configured to receive, in particular through a public computer network NW, and to store the dosage information from the electronic programming computer 70 and the intake information from the device 1;
- an electronic computer 90 configured to communicate with the remote server 80, in particular through a public computer network NW, and to access the dosage information and the intake information.

One further aspect of the present invention refers to a tablet blister accessory comprising a device 1 as described above.

Figure 10:
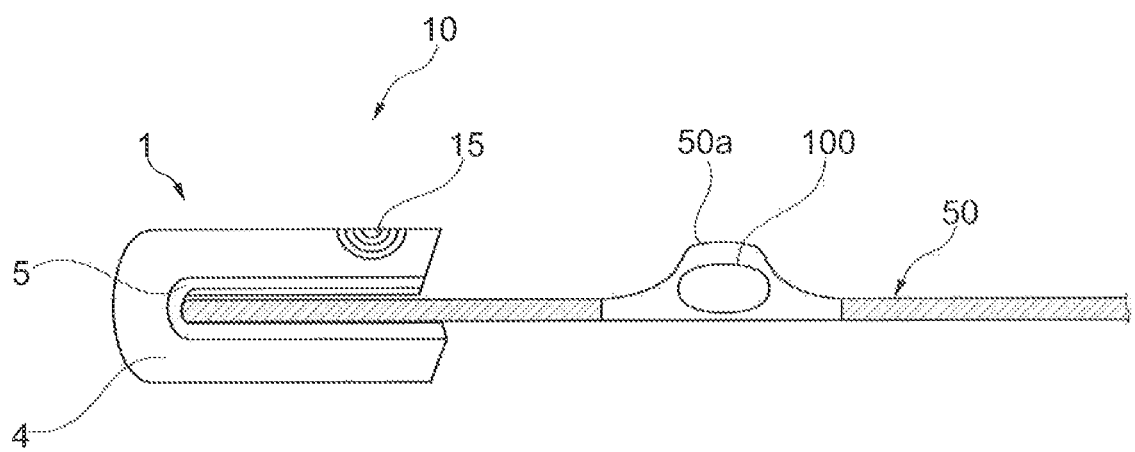
FIG. 10 shows another embodiment of the device of FIG. 4.

FIG. 10 shows an embodiment of such a tablet blister accessory comprising a device 1 described above. The blister comprises an outer case 4 adapted to become integral with a drug blister. Typically, the drug blister 50 has a planar surface and one or more lidding foil 50a to define an housing to accommodate a corresponding tablet. The lidding foil 50a is usually an aluminum foil thermo-welded on the planar surface. To better adhere to the planar surface of drug blister 50, the outer case 4 of the tablet blister accessory 10 comprises an anti-slip layer 5 that contacts the surface of the drug blister 50, when the accessory is applied to it.

In one embodiment, the sensor means of the device 1 of the tablet blister accessory 10 are adapted to detect vibrational energy transferred to the drug blister 50, when a user extracts a tablet from the blister. In particular when the user transfers energy to the blister to tear part of the surface beneath the lidding foil 50a covering the tablet. The processor 25 is configured to detect vibration energy according to embodiments described above, in particular with reference to FIG. 7.

One further aspect of the present invention refers to a liquid drug injection pen accessory comprising a device 1 as described above.

Figure 11:
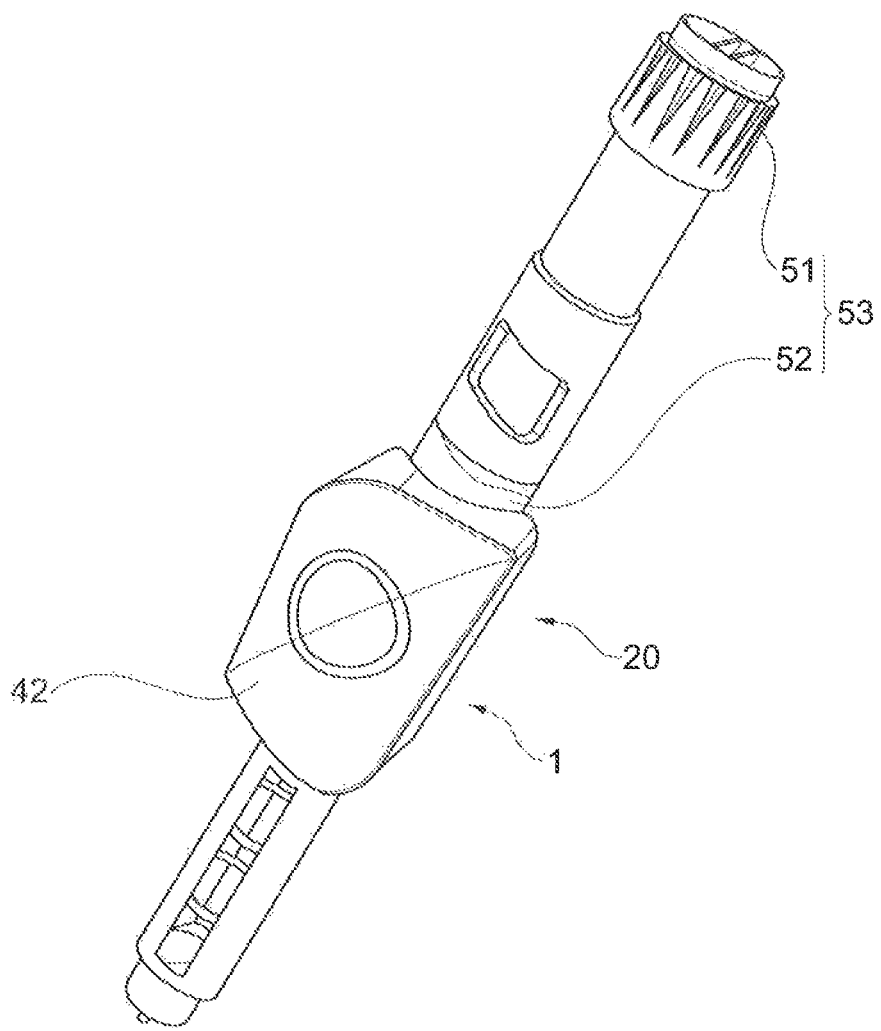
FIG. 11 shows a perspective view of an embodiment of device according the present invention applied to a liquid drug injection pen.

FIG. 11 shows an embodiment of such a liquid drug injection pen accessory. A liquid drug injection pen is a device adapted to contain, dose and assume a liquid drug. For example, such a liquid drug injection pen is an insulin injection pen. Such a pen has tubular shape defining a housing for a vial containing the liquid drug. On the top, the pen has a charge and release mechanism. Typically, the charge mechanism comprises a gear rotatable around an axis. One or more doses of drugs are set rotating the gear of a corresponding angular quantity. The user/patient is aided during this process by a graphical indicator on the gear that shows how many doses are set. Furthermore, the gear produces a click for each dose charged. The click is due to a mechanical action of an inner toothed wheel whose retrograde motion is prevented by a small harpoon. When the user rotates the gear, the harpoon produces a click for each tooth of the inner wheel that, during rotation, in sequence engages. Once the number of doses is set, the patient assume the liquid drug acting on the release mechanism. Typically, the release mechanism comprises a button movable along an axis from a raised position to multiple release positions. The number of positions in which the release button lowers is equal to the number of doses previously charged with the gear.

Figure 12:
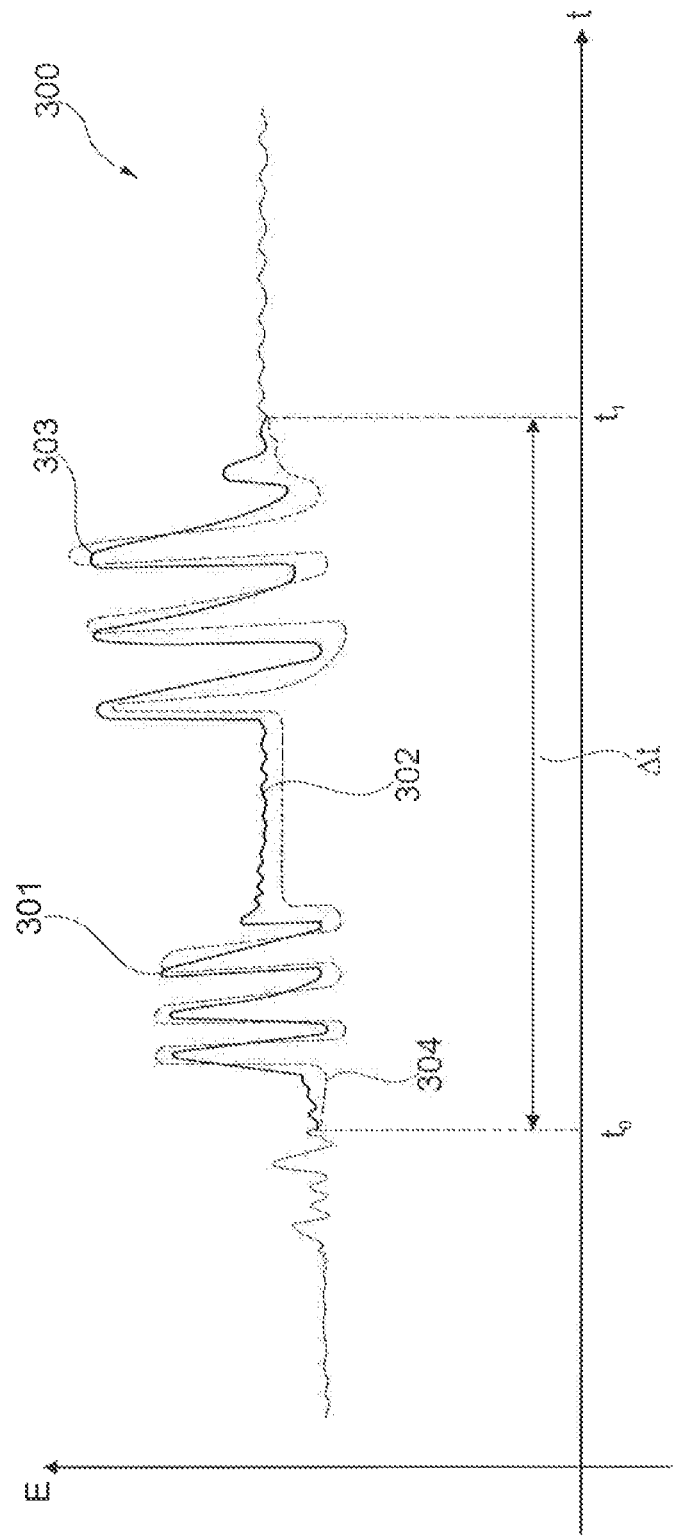
FIG. 12 shows a diagram of the vibrational energy detected by the device of FIG. 11 in response to interactions of a user assuming a drug using such a injection pen.

In one embodiment, the accelerometer of the device 1 detects the vibrational energy transferred to the injection pen during the charge phase, and the vibrational energy during the release phase. In other words, the accelerometer detects the vibrational energy that the user transfers to the injection pen through the rotation of the gear to set a certain number of doses, and detects the vibrational energy that a user transfers to the injection pen through the pressure on the release button. According to one embodiment, the processor 25 is configured to calculate intake information on the basis of the vibrational energy that the user transfers to the injection pen through the rotation of the gear to set a certain number of dose, and on the basis of the vibrational energy that the user transfers to the injection pen through the pressure on the release button. FIG. 12 shows a diagram 300 of the vibrational energy detected by sensor means of the accessory of FIG. 11. On the basis of data represented in such diagram, the processor 25 calculates intake information.

In particular, as shown in FIG. 12 the part of the diagram indicated with the reference number 301 is relative to the charge phase. The part indicated with the reference number 303 is relative to the release phase. The processor 25 sets a time lapse Δt accordingly, to obtain all the vibrational energy from the accelerometer transferred during the charge and release phases.

It is to be noted that from the charge phase to the release phase, the user/patient typically turns the injection pen to inject the drug properly. Through the package information, this feature of the assumption process may be taken in due account when the intake information are calculated.

According to one embodiment, the device 1 of the accessory described comprises a gyroscope. According to one embodiment, if package information reports that the injection pen is under use, the processor 25 is configured to evaluate also the orientation information. In particular, the orientation information considered are the ones in the time frame within the vibrational energy data 301 and 302. In fact, in this time frame a change in the orientation of the injection pen is expected, the processor 25 is thus configured to check if orientation information reflect this change. As already described the intake information may be calculated assessing the difference between absolute value of data of the reference diagram (dashed, 304) and data of the vibrational energy detected (indicated as 301, 302 and 303). In one embodiment, the processor 25 is configured to calculate also if all the doses of drug are assumed. For example, the processor 25 may calculate if the number of maximums values of the part 301 of the diagram corresponds to the number of maximums values of the part 303 of the diagram, and thus determine how many doses have been skipped.

One further aspect of the present invention refers to a tablet bottle accessory comprising a device 1 as described above.

Figure 13:
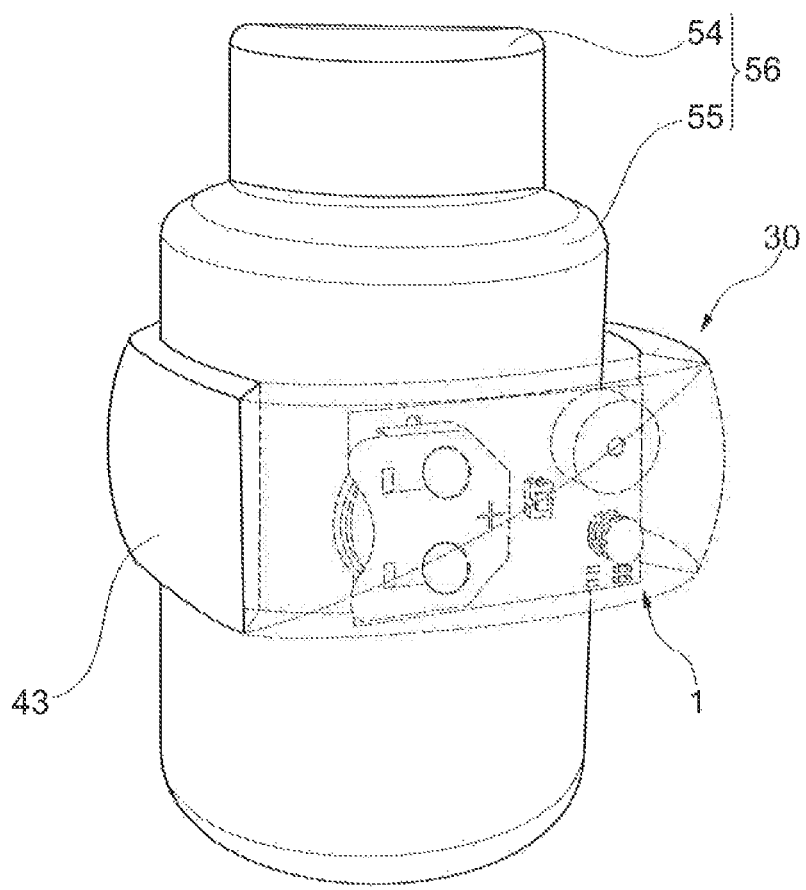
FIG. 13 shows an embodiment of a tablet bottle accessory according the present invention.

FIG. 13 shows an embodiment of such a tablet bottle accessory comprising a device 1 as described above.

Typically, a tablet bottle 56 comprises a containment body 54 wherein the tablets are stored and a safety cap 54 screwed on the containment body 55 that closes it. According to one embodiment, the tablet bottle accessory 30 comprises an outer casing 43 adapted to become integral with the tablet bottle 56. In one embodiment, such outer casing has circular shape adapted to surround a portion of the containment body 55.

The sensor means of the device 1 are adapted to detect vibrational energy transferred to the tablet bottle when a user extracts a tablet from the bottle. In one embodiment, the sensor means of the device 1 comprise an accelerometer and a gyroscope.

The processor 25 is configured to calculate intake information on the basis of vibrational energy detected by the accelerometer of the device 1, and on the basis of orientation information provided by the gyroscope of the device 1. To take a tablet contained in a tablet bottle 56, the user unscrews the safety cap 54 applying a certain force, rotates the containment body 55 and extracts the tablet(s), typically shaking the containment body 55 to let the tablet spills out. The processor 25 is configured to calculate intake information on the basis of the corresponding vibrational energy and orientation detected.

One further aspect of the present invention refers to drug inhaler accessory comprising a device 1 as described above.

Figure 14:
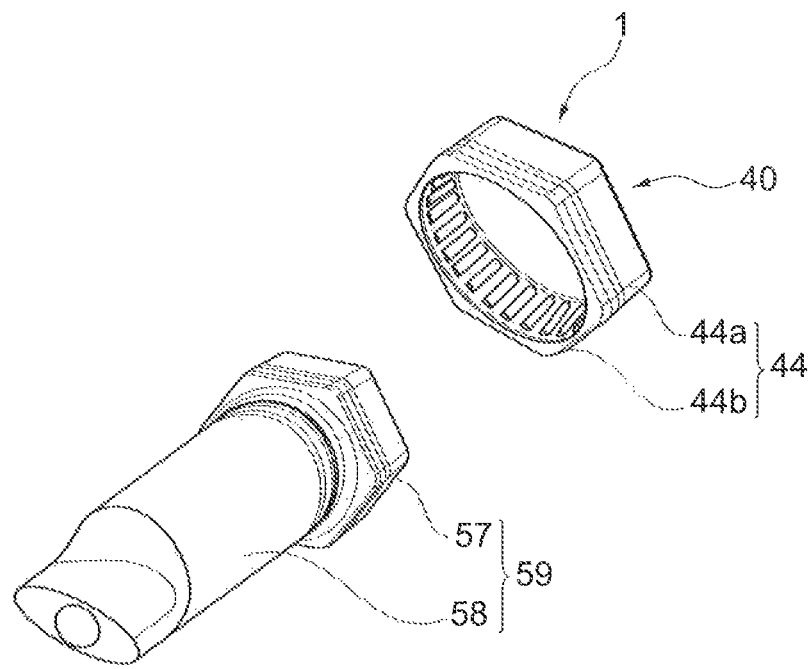
FIG. 14 shows an embodiment of a drug inhaler accessory according the present invention.

FIG. 14 shows an embodiment of such a drug inhaler accessory. The drug inhaler of this embodiment may be, for example, the one known with the trade name "Turbohaler" of AstraZeneca.

Typically, a drug inhaler 59 comprises an activation mechanism 57 and an expansion chamber 58. The activation mechanism 57 charges the drug in the expansion chamber. The activation mechanism 57 comprises a gear operatively coupled to a spring (or a mechanism with a similar function). The user/patient rotates the gear to activate the spring for charging the drug in the inhalation chamber. After this actions, the user may assume the drug inhaling from the mouthpiece 58*b* at one end of the expansion chamber.

In one embodiment, the device comprises an outer casing 44 adapted to become integral with an outer casing 57 of a drug inhaler. In particular the outer casing 44 has an outer shape 44*a* similar to the outer shape of the activation mechanism 57. Furthermore, the outer casing 44 has a room 44*b* adapted to receive the activation mechanism 57. The user/patient acts on the outer casing 44, that covers the activation mechanism 57, to charge the drug in the expansion chamber.

Figure 15:
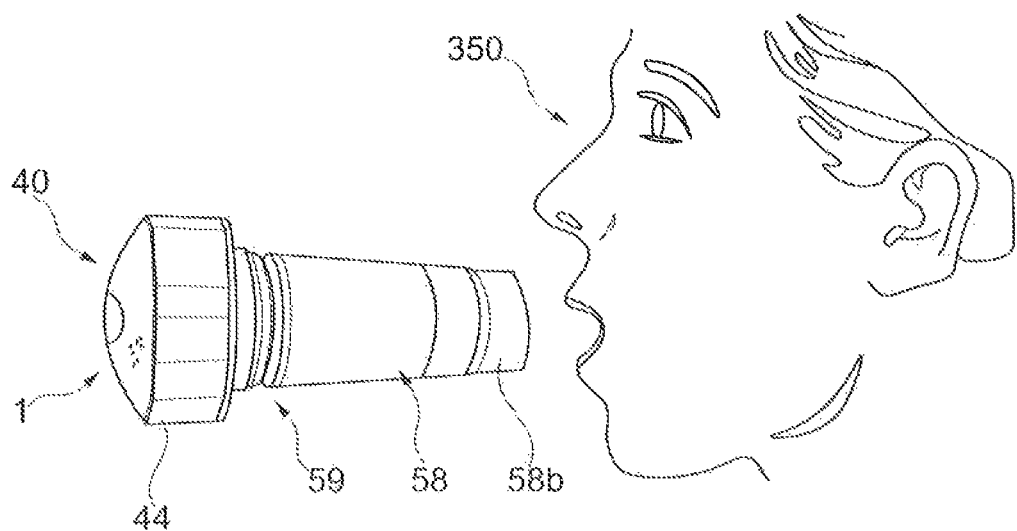
FIG. 15 show interactions of a user with a drug inhaler comprising the drug inhaler accessory of FIG. 14 to assume one or more doses of the drug contained.

FIG. 15 shows an embodiment of a drug inhaler accessory applied on a drug inhaler 59. The patient 300 assumes the drug in the inhalation chamber 58 inhaling from the mouthpiece 38, for an amount of time sufficient to inhale the drug in the expansion chamber 58.

Figure 16:
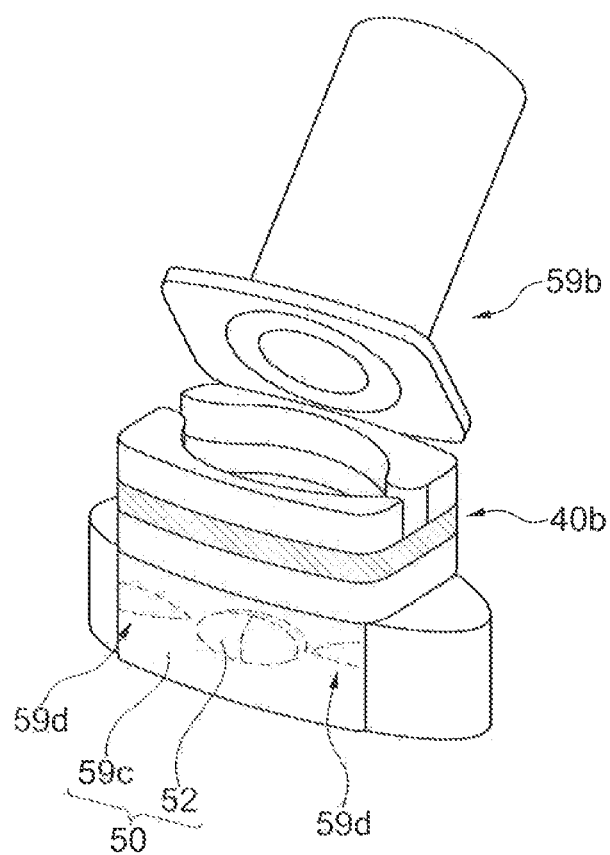
FIG. 16 shows an alternative embodiment of the drug inhaler accessory of FIG. 14.

FIG. 16 shows another embodiment of a drug inhaler accessory 40*b*. The drug inhaler 59*b* comprises a containment 59*c* for a capsule 52 containing powder to be inhaled by a patient. According to this embodiment, the package 50, with which the user interacts to release one dose of a drug, comprises the capsule 52 and the containment 59*c*.

The drug inhaler of this embodiment may be, for example, the one known with the trade name "Seebri Breezhaler" of Novartis.

To inhale (assume) the drug, the patient acts on the activation mechanism 59*d*. Such activation mechanism comprises two buttons at two opposite ends of the containment 59*c* respectively connected at two piercing devices. By means of the two buttons, the piercing devices are approached towards the capsule 52 until they break such capsule.

As shown in FIG. 16, the patient inserts the capsule 52 containing the powder to inhale into the containment 59*c*.

Figure 17:
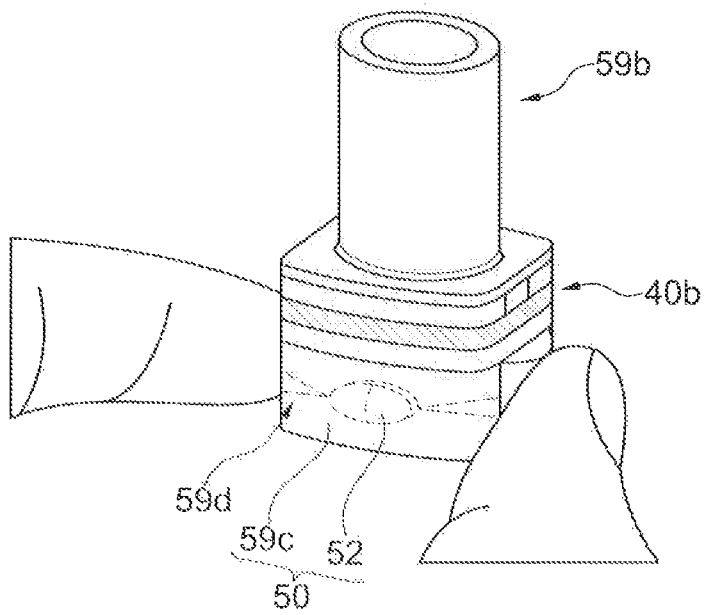
FIG. 17 show interactions of a user with a drug inhaler comprising the drug inhaler accessory of FIG. 16 to assume one or more doses of the drug contained.

FIG. 17 shows typical actions of a patient aimed at releasing the dose of powder. As shown, the patient breaks the plastic shell of the capsule 52 by means of the activation mechanism 59*d*. In particular, when the piercing devices break the capsule 52, a corresponding vibrational energy is produced. The device 1 integrated in the inhaler accessory 40*b* detects such vibrational energy to establish if the drug may be deemed assumed.

Figure 18:
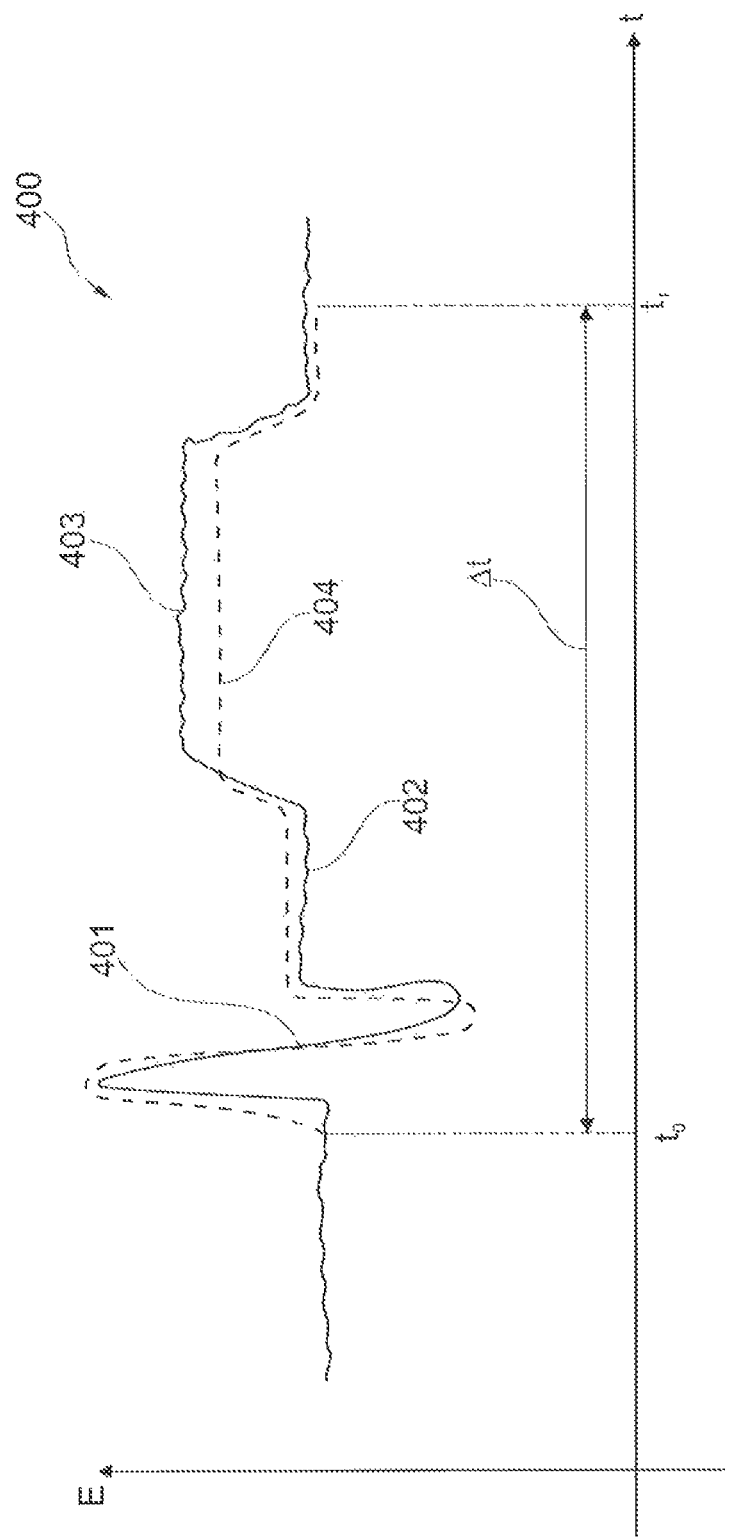
FIG. 18 shows a diagram of the vibrational energy detected by the device of FIG. 15 in response to interactions of the user assuming the drug.

FIG. 18 shows a diagram 400 of the vibrational energy detected by sensor means of the accessory of the FIGS. 14 and 15. On the basis of data represented in such diagram, the processor 25 calculates intake information.

In particular, as shown in FIG. 16 the part of the diagram indicated with the reference number 401 is relative to the charge phase, that indeed occurs in a very quick way. The part indicated with the reference number 403 is relative to the inhale phase of the drug by the patient. The processor 25 sets a time lapse Δt accordingly, to obtain all the vibrational energy from the accelerometer transferred during the charge and inhalation phases.

It is to be noted that from the charge phase to the inhalation phase, the user/patient typically turns the inhaler to inhale the drug properly (as represented in FIG. 15). Through the package information, this feature of the assumption process may be taken in due account when the intake information are calculated. According to one embodiment, the device 1 of the accessory described comprises a gyroscope. According to one embodiment, the processor 25 is configured to evaluate also the orientation information if the package information reports that a drug inhaler is under use. In particular, the orientation information considered are the ones in the time sub-frame within the vibrational energy data 401 and 402. In fact, in this time sub-frame a change in the orientation of the inhaler pen is expected, the processor 25 is thus configured to check if orientation information reflect this change. As already describe the intake information may be calculated assessing the difference between absolute value of data of the reference diagram (dashed, 304) and data of the vibrational energy detected (indicated as 401, 402 and 403).

FIGS. from 19 to 22 show another embodiment of a device 1 according the present invention. In this embodiment, the device 1 is applied to the outer box 50 (known in field as "second package") containing a drug, and the sensor means are to detect movements of such box and any associated vibrations. The processor 25 is configured to calculate intake information on the basis of movements and any associated vibrations of the box detected by the sensor means.

Figure 19:
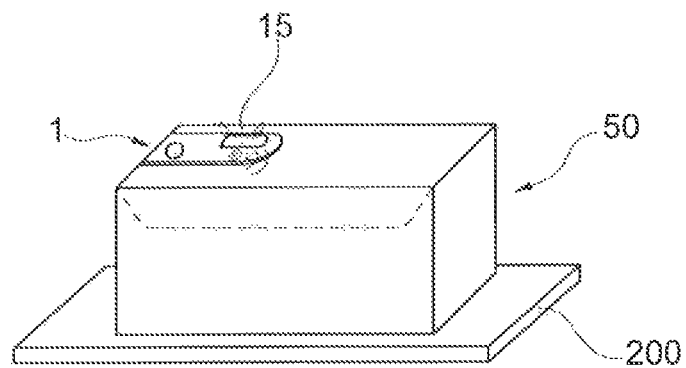
Figure 20:
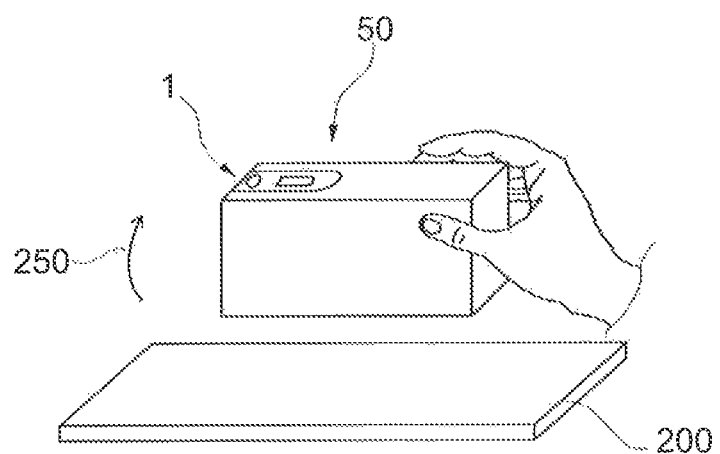
Figure 21:
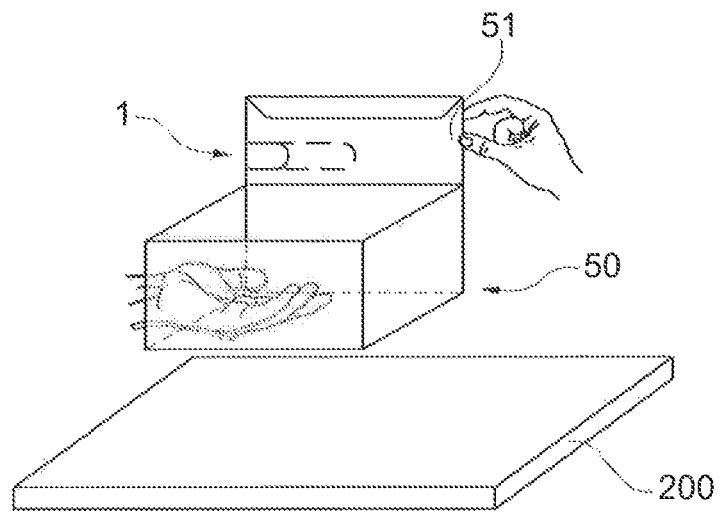
Figure 22:
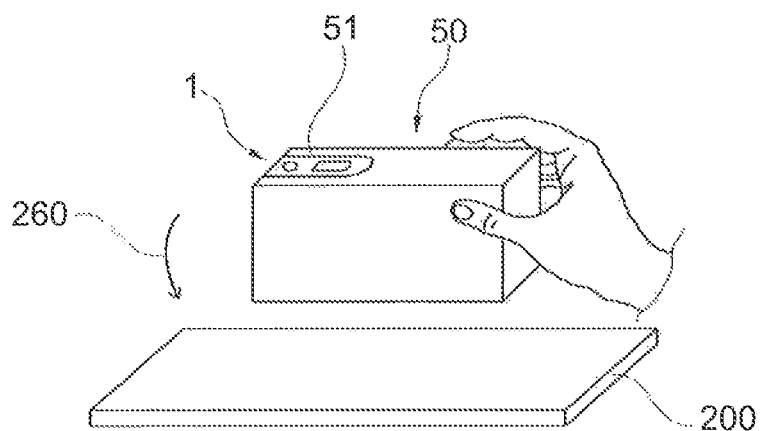

In FIG. 19 the box 50 lays on a surface 200 and the signaling means 15 signal an item of the dosage information. In FIG. 20 a user raises the box 50 according direction 250 from the surface 200. The device 1 is applied to the opening tab 51 of the box 50. In FIG. 21 the user opens the opening tab 51 to extract the dose of drug he has to assume, and in FIG. 22 closes the opening tab 51 and returns the box on the surface 200, according the direction 260. The sensor means detect the movements and any associated vibrations related to these actions and the processor 25 calculate intake information accordingly.

The invention claimed is:

1. A device for controlling the intake of drugs, applicable to a package containing one or more doses of a drug, said device comprising:
    sensor means adapted to detect the vibrational energy transferred to said package, in response to interactions of a user with said package to release one or more doses of said drug;
    a processor connected to said sensor means;
    wherein said processor is configured to calculate intake information of said drug on the basis of the vibrational energy detected by said sensor means;
    wherein said sensor means comprise at least one accelerometer implemented as a micro-electro-mechanical system;
    wherein said processor is configured to obtain from said accelerometer the vibrational energy detected in a time frame.

2. The device according to claim 1 further comprising:
    first storage means adapted to store dosage information of said drug, said dosage information being related to a patient;
    first communication means, in particular for proximity communications, adapted to receive said dosage information;
    second storage means adapted to store intake information of said drug by said patient, calculated by said processor.

3. The device according to claim 2, wherein said processor is configured to receive said dosage information by means of said first communication means from an electronic programming computer.

4. The device according to claim 3, further comprising second communication means, and wherein said processor is further configured to transmit said dosage information and said intake information to a remote server by means of said second communication means, in particular via a public information network (NW).

5. The device according to claim 3, wherein said dosage information comprise package information relative to the type of package containing said one or more doses of a drug.

6. The device according to claim 1 further comprising signaling means connected to said processor, and wherein said processor is further configured for signaling an item of said dosage information via said signaling means.

7. The device according to claim 6, wherein said processor is further configured to iterate the signaling of said item of said dosage information on the basis of said intake information calculated.

8. The device according to claim 1, wherein said time frame is set on the basis of said package information and wherein said processor is further configured to calculate intake information also on the basis of said package information.

9. The device according to claim 1, wherein said sensor means further comprise a gyroscope adapted to provide orientation information on the orientation of said package.

10. The device according to claim 9, wherein said processor is configured to calculate intake information on the basis of said vibrational energy, detected by said accelerometer, and said orientation information.

11. The device according to claim 10, wherein said processor is configured to evaluate said vibrational energy detected by said accelerometer and/or said orientation information on the basis of said package information for calculating said intake information.

12. The device to claim 1, comprising an outer casing adapted to become integral with said package.

13. A system for signaling the intake of drugs, comprising;
- a device according to claim 1, in particular comprising first communication means;
- a signaling device comprising signaling means and second communication means;
wherein said processor of said control device is configured to transmit dosage information by means of said communication means of said device to said signaling device; and wherein said signaling device is adapted to receive dosage information by means of the second communication means and to signal items of said dosage information by means of its signaling means.

14. The system according to claim 13, wherein said device comprises or consists of an element wearable by said patient.

15. A system for controlling the intake of drugs, comprising;
- a device according to claim 1, in particular comprising communication means;
- an electronic programming computer configured to generate dosage information related to a patient and to transmit said information to said device;
- a remote server configured to receive, in particular through a public computer network (NW), and to store said dosage information from said electronic programming computer and said intake information from said device;
- an electronic computer configured to communicate with said remote server, in particular through a public computer network (NW), and to access said dosage information and said intake information.

16. Tablet blister accessory comprising a device according to claim 1.

17. Tablet bottle accessory comprising a device according to claim 1.

18. Liquid drug injection pen accessory comprising a device according to claim 1.

19. Drug inhaler accessory comprising a device according to claim 1.

20. The device according to claim 1, wherein said processor is configured to calculate intake information of said drug on the basis of vibrational energy detected by said sensor means during release of at least one drug dose.

21. The device according to claim 1, wherein said processor is configured to calculate intake information of said drug also on the basis of vibrational energy detected by said sensor means during a charge phase.

* * * * *